United States Patent [19]

Spicer et al.

[11] Patent Number: 5,340,584

[45] Date of Patent: * Aug. 23, 1994

[54] METHODS AND FORMULATIONS FOR USE IN INHIBITING CONCEPTION AND IN TREATING BENIGN GYNECOLOGICAL DISORDERS

[75] Inventors: Darcy V. Spicer, Pasadena; Malcolm C. Pike, Long Beach, both of Calif.

[73] Assignee: University of Southern California, Los Angeles, Calif.

[*] Notice: The portion of the term of this patent subsequent to May 18, 2010 has been disclaimed.

[21] Appl. No.: 952,513

[22] PCT Filed: Apr. 10, 1992

[86] PCT No.: PCT/US92/02973

§ 371 Date: Feb. 1, 1993

§ 102(e) Date: Feb. 1, 1993

Related U.S. Application Data

[63] Continuation-in-part of Ser. No. 684,612, Apr. 12, 1991, abandoned.

[51] Int. Cl.$^5$ .............. A61F 2/02; A61F 6/06; A61K 37/38; A61K 9/50

[52] U.S. Cl. .............. 424/426; 424/423; 424/424; 424/430; 424/432; 424/433; 424/484; 424/485; 424/486; 424/487; 424/488; 424/489; 424/DIG. 14; 424/449; 424/451; 514/800; 514/841; 514/842; 514/843

[58] Field of Search .............. 424/422, 423, 424, 426, 424/430, 432, 433, 484, 485, 486, 487, 488, 489, 490, 496, 497, 498, DIG. 14; 514/2, 12, 21, 800, 841, 842, 843; 530/313, 850, 853; 128/830, 832, 833

[56] References Cited

PUBLICATIONS

Watts et al., "Effects of Oral Estrogens and Esterified Estrogens & Androgen on Bone Mineral Density in Postmenopausal Women", The 2nd Annual Meeting North American Menopause Society Program, S-F16, Sep. 25-28, 1991.

Bergkvist, et al. N.E. Journal of Medicine 321: 293-97 (1989).
Conn et al. N.E. Journal of Medicine 324: 93-103 (1991).
Donnez et al. Fertility and Sterility 51: 947-50 (1989).
Cowsar et al. Long Acting Contraceptive Delivery Systems pp. 145-162 (eds. Zatuchni et al. 1984).
Ferguson et al. Journal of Controlled Release 8: 45-54 (1988).
Friedman Fertility and Sterility 51: 526-28 (1989).
Garza-Flores et al. Contraception 30: 371-79 (1984).
Gilley et al. Southern Research Inst. 73-73.
Hahn et al. Long Acting Contraceptive Delivery Systems, pp. 97-112 (eds. Zatuchni et al. 1984).
Hsieh et al. Rutgers Univ. pp. 134-135.
Hsieh et al. Drug Development and Industrial Pharmacy II(6&7): 1391-1410 (1985).
Kaufmann et al. Journal of Clinical Oncology 7: 1113-1119 (1989).

Primary Examiner—Thurman K. Page
Assistant Examiner—Carlos Azpuru
Attorney, Agent, or Firm—Robbins, Berliner & Carson

[57] ABSTRACT

Compositions and methods which are effective to inhibit conception and to treat benign gynecological disorders for extended periods of time are described, wherein an effective amount of a gonadotropin hormone releasing hormone composition and an effective amount of an estrogenic composition are provided over a first period of time, in addition to a progestogen and optionally an androgenic composition. According to one protocol, the progestogen is provided for a second, shorter period of time; the progestogen is provided at a higher level for at least 5 to about 20 days, and then at a lower level for the remainder, if any, of the second period of time. In an alternative protocol, the progestogen is provided at a lower level substantially throughout the period of administration of gonadotropin hormone releasing hormone composition and estrogenic composition. An effective amount of the androgenic hormone is optionally provided over the first period of time.

32 Claims, No Drawings

METHODS AND FORMULATIONS FOR USE IN INHIBITING CONCEPTION AND IN TREATING BENIGN GYNECOLOGICAL DISORDERS

This application is a continuation-in-part of Ser. No. 07/684,612 filed Apr. 12, 1991, now abandoned.

BACKGROUND OF THE INVENTION

This invention relates to methods for inhibiting conception in mammals and for treating benign gynecological disorders, as well as to formulations for use in such methods. More particularly, the present invention is directed to methods and preparations effective in inhibiting conception and in treating benign gynecological disorders, including premenstrual syndrome, for extended periods of time.

Gonadotropin releasing hormone (GnRH), also known as luteinizing hormone releasing hormone (LHRH), produced by the hypothalamus controls the secretion of follicle stimulating hormone (FSH) and luteinizing hormone (LH) by the pituitary and thence gonadal steroid hormone production. Potent synthetic agonists of GnRH administered to premenopausal women have been shown to produce a transient rise in FSH/LH release followed by a sustained suppression. Immediately after GnRH agonists became available in the late 1970s, a number of approaches to the use of a GnRH agonist as a contraceptive were explored. Among these approaches, inhibition of ovulation by the chronic administration of GnRH agonists appeared to offer the greatest potential. It was hoped that GnRH agonists would form the basis of an improved method of contraception by offering greater convenience, increased effectiveness or fewer side effects than is the case with combination-type oral contraceptives (COCs).

Inhibition of ovulation by GnRH agonists has been found, as expected, to be dose-related. When administered in a dose just high enough to ensure anovulation, the ovaries may continue to produce estrogen. This is an unstable situation, with different women having widely varying serum estrogen levels. There has also been concern that endometrial hyperplasia would occur in some women, while in others there would be periods of hypoestrogenemia with unacceptable vasomotor symptoms and probably loss of bone mineral content.

"High-dose" GnRH agonists have been observed to uniformly reduce serum estradiol and serum progesterone to oophorectomized levels. The development of "high dose" depot formulations of GnRH agonists permits sustained inhibition of ovulation and suppression of ovarian steroid production, as well as improved ease of drug administration. The treatment is reversible; in a study of 50 patients, recovery of menstrual function occurred on average at 87 days (range 44–126 days) following 6–8 months treatment with the GnRH agonist tryptorelin [Zorn, J. -R. et al., Fertil.Steril. 53:401–06 (1990)]. Other depot formulations of GnRH agonists produce similar sex-steroid suppression including decapeptyl [George, M. et al., Int.J.Fertil. 34:19–24 (1989)], goserelin [Kaufman, M. et al., J.Clin.Oncol. 7:1113–19 (1989)] and buserelin [Donnez, J. et al., Fertil.Steril. 51:947–50 (1989)].

In spite of their clear effectiveness as contraceptive agents, side effects attendant to the use of "high-dose" GnRH agonists for prevention of pregnancy has prevented their general adoption. Common side effects reported to occur with depot GnRH agonists in premenopausal patients include: hot flashes, vaginal dryness, irregular vaginal bleeding and fatigue. Additional side effects that have been reported in some patients receiving GnRH agonists include: sweating, headache, depression, lability in mood, nausea and/or vomiting, nervousness, insomnia, pollakisuria, weight gain, sleepiness, dizziness, decreased libido and mild breast tenderness or swelling.

A recent review article reflects current thinking about GnRH and its analogues (Conn, P. M. and Crowley, Jr., W. F., "Gonadotropin-Releasing Hormone and Its Analogues," N.Engl.J.Med. 324:93–103 (1991)). The authors note at pages 96–97 that "whether to supplement GnRH-agonist analogues with sex steroids is a complex decision"; they propose estrogen replacement followed by the administration of a progestational agent "at physiologic doses and in a physiologic (i.e., sequential) pattern."

U.S. Pat. No. 4,762,717 to Crowley, Jr., the entire disclosure of which is hereby incorporated by reference, is based on the above-noted assumption that administration of a progestational agent should be effected in a sequential pattern so as to mimic the phases of the menstrual cycle. The patent describes contraceptive methods for female animals using luteinizing hormone releasing hormone (LHRH) compositions in combination with sex steroids. The patent calls for administering LHRH (or analogs, agonists or antagonists thereof) in a first delivery system combined with continuous administration of an effective amount of estrogenic steroids during the "follicular phase" of the menstrual cycle beginning at the onset of "normal menses". A second delivery system is administered during the "luteal phase" of the menstrual cycle until the onset of "normal menses". The second delivery system comprises the LHRH/estrogenic steroid combination and additionally provides an effective dosage of a progestational steroid.

This administration sequence is designed to mimic the physiological secretion of steroids in the menstrual cycle. As a consequence, each delivery system is effective for a period of only about two weeks (corresponding to the typical length of each of the follicular and luteal phases, according to the designation of Crowley).

The approach of Crowley is clearly unacceptable when considered in light of current knowledge about the long-term effects of administering the components thereof for the periods of time specified. The proposed level of estrogen administration (i.e., to achieve an estradiol concentration of about 50 to about 140 pg/ml for a human female) in the two delivery system approach of Crowley is unnecessarily high and the proposed amount of progestogen to be administered unnecessarily high. Epidemiologic case-control studies of postmenopausal breast cancer risk and estrogen replacement therapy (ERT) using population controls suggest that increased exposure to exogenous estrogen leads to an increased risk of breast cancer in a dose-dependent fashion. Moreover, administration of progestational steroid for about two weeks of every approximately 28-day treatment cycle was associated with unacceptable risks to the patient in a recent epidemiological study [Bergkvist, L. et al., N.Engl.J.Med. 321:293–97 (1989)]; the study suggests that the addition of progestogen during the latter half of the 28-day ERT cycle may double the risk associated with use of estrogen alone.

Pike, M. C. et al., *Br. J. Cancer* 60:142–48 (1989), the entire disclosure of which is also hereby incorporated by reference, have proposed a contraceptive regimen in which "high-dose" LHRH agonist treatment is coupled with estrogen replacement therapy (ERT), specifically 0.625 mg of conjugated equine estrogens for 21 days in each 28-day treatment cycle. The administration of a progestational steroid is proposed to be limited to a 10–16 day interval every three or four cycles. It is now clear that the 7-day period in each treatment cycle when ERT is not provided would be associated in many patients with symptoms of estrogen withdrawal, such as hot flushes. Moreover, a negative calcium balance could develop during the period of hypoestrogenemia with the possibility of resultant osteoporosis. Finally, blood cholesterol levels would likely be adversely affected during that time. Therefore, it is unlikely that the specific regimen proposed by Pike et al. would be found acceptable.

Administration of various compositions comprising sex hormones has also been contemplated in connection with the treatment of various benign gynecological disorders, such as endometriosis, fibroids and polycystic ovarian syndrome. One particularly prevalent disorder for which hormonal therapy has been contemplated is late luteal phase dysphoric disorder (commonly referred to as premenstrual syndrome). The essential feature of late luteal phase dysphoric disorder is a pattern of clinically significant emotional and behavioral symptoms that occur during the last week of the luteal phase and remit within a few days after the onset of the follicular phase. In most females, these symptoms occur in the week before and remit within a few days after the onset of menses. Non-menstruating females who have had a hysterectomy but retain ovarian function may also report similar symptoms. Among the most commonly experienced symptoms are the following: marked affective lability (e.g., sudden episodes of sadness or irritability); persistent feelings of irritability, anger or tension; feelings of depression and self-deprecating thoughts; decreased interest in usual activities; fatigue and loss of energy; a subjective sense of difficulty in concentrating; changes in appetite; cravings for specific foods; sleep disturbance; breast tenderness or swelling; headaches; joint or muscle pain; a sensation of bloating; and weight gain. The symptoms are often so severe as to seriously interfere with work or with usual social activities or relationships with others.

It has been reported that administration of a GnRH agonist may ameliorate some of the symptoms of premenstrual syndrome [Mortola, J. F. et al., *J. Clin. Endocrin. & Metab.* 72:252A–252F (1991)]. In addition to administration of GnRH agonist alone, the study included in a 28-day regimen combinations of GnRH agonist with conjugated equine estrogen (CEE) on days 1–25, with medroxyprogesterone acetate (MPA) on days 16–25, and with both CEE on days 1–25 and MPA on days 16–25. The authors concluded that the use of 0.625 mg CEE on days 1–25 and 10 mg MPA on days 16–25 would provide a safe and effective method of obtaining the beneficial effects of GnRH agonist on premenstrual syndrome. Unfortunately, this type of regimen (calling for addition of progestogen during the latter half of each 28-day ERT cycle) for treatment of premenstrual syndrome would be subject to the same objections previously noted for comparable contraceptive regimens, i.e., a possible doubling of the breast cancer risk associated with use of estrogen alone (Bergkvist et al., supra).

It is an object of the present invention to provide a contraceptive regimen which would obviate a number of problems attendant to the use of existing methods of birth control, while at the same time reducing the risk of adverse consequences associated with the heretofore known methods.

It is a further object of the invention to provide methods and formulations which are useful in treatment of benign gynecological disorders.

BRIEF DESCRIPTION OF THE INVENTION

In accordance with the present invention, there are provided compositions and methods for preventing pregnancy in a mammal (in particular, a human female) and for treating benign gynecological disorders, wherein a GnRH composition, an estrogenic composition, a progestogen, and optionally an androgenic composition are administered according to specific protocols as defined herein. In all of these protocols, over a first period of time (on the order of about 2 to about 6 months), a GnRH composition is administered in an amount effective to suppress ovarian estrogen and progesterone production, thereby inhibiting ovulation. Over this first period of time, in all protocols an amount of an estrogenic composition effective to prevent symptoms of estrogen deficiency is also administered; the symptoms of estrogen deficiency which may develop during prolonged therapy with a GnRH composition include, but are not limited to, symptoms of the menopause, vasomotor instability, harmful alterations in serum cholesterol or its fractions, and urogenital atrophy. In addition to the GnRH composition and the estrogenic composition, a progestogen is provided. Pursuant to a first embodiment of the invention, the progestogen is administered only for a second, shorter period of time concurrent with the first period of time (on the order of about five to about 90 days, generally less than about $\frac{1}{4}$ to about $\frac{1}{2}$ of the term of administration of the GnRH composition and estrogenic composition); in this embodiment, administration of the progestogenic composition is carried for at least 5 to about 20 days in an amount effective to induce a secretory endometrium, followed by a lower amount effective to decrease endometrial cell proliferation for the remainder, if any, of the period of progestogen administration. Pursuant to an alternative embodiment of the invention, progestogen administration is carried out throughout the entire first period of time at the lower amount effective to decrease endometrial cell proliferation. Optionally in either protocol, an androgenic composition is administered over the first period of time in conjunction with the administration of the GnRH composition, estrogenic composition and progestogen as previously described. The androgenic composition is administered in an amount effective to restore a patient's effective androgen level to a normal premenopausal level, and in particular to maintain bone mineral density.

Use of delivery systems for long-term release of GnRH agonists, requiring infrequent administration, makes the inventive regimens both practical and potentially more effective in preventing conception and/or treating various benign gynecological disorders. As ovulation would be prevented by the GnRH agonist, the amount of add-back compositions administered is substantially reduced from amounts typically employed in conventional COCs. Moreover, in accordance with the present invention the levels of estrogen replacement would be significantly lower than those proposed as suitable in human female patients by Crowley. Further, the administration of substantial amounts of progestational composition would not be effected every 28-day cycle, as proposed by Crowley; rather, either an amount of progestational composition sufficient to induce a secretory endometrium would be provided only for a relatively short time interval over each extended period of time (pursuant to one embodiment of the invention), or the amount of progestogen provided continuously throughout the regimen would be substantially lower (pursuant to a second, alternative embodiment of the invention).

The regimens of the present invention exhibit greater contraceptive effectiveness than currently available contraceptive protocols (such as the use of COCs) and are also effective in treating several benign gynecological disorders, including but not limited to late luteal phase dysphoric disorder (premenstrual syndrome), fibroids, endometriosis and polycystic ovarian syndrome. In addition, the use of a long-term administration depot provides significantly greater convenience of administration. The reduction in the amount of compositions administered also has the effect of reducing the projected rate of incidence of breast cancer, as well as reducing the incidence of various benign gynecological disorders. The invention further reduces the risk of ovarian cancer, as is known to occur with COC use.

DETAILED DESCRIPTION OF THE INVENTION

Pursuant to the present invention, the regimen of the present invention comprises a slow-release (or depot) formulation which is effective for an extended period of time. This extended period of time is substantially longer than is the case with either delivery system of Crowley, each of which is designed to be replaced after only a two-week period. Typically, the depot formulation of the invention is effective over an extended period of time of at least about two months. Depending on the composition and mode of administration, the inventive formulation may be effective for as long as about six months or more. It is presently preferred that the formulation be effective over about a three or four month period.

A number of compounds have been developed to inhibit effective release or action of gonadotropin releasing hormone (GnRH), including both agonists and antagonists of GnRH. While the following detailed disclosure describes in particular the use of GnRH agonists, other GnRH analogues (such as GnRH antagonists) and GnRH itself may also be employed in a manner known per se for essentially complete suppression of LH and FSH in formulations in accordance with the invention, and are hereinafter referred to as "GnRH compositions." The GnRH compositions provide continuous suppression of pituitary gonadotropin secretion, thereby inhibiting ovulation.

A GnRH agonist formulation, leuprolide acetate depot (LAD), is commercially available in the United States and lasts about 4 weeks. A 16-week formulation of buserelin has been tested [Donnez, J. et al., Fertil. Steril. 51:947–950 (1989)]. Longer acting formulations of leuprolide acetate or other gonadotropin compositions are also contemplated as within the scope of the invention. Other suitable GnRH compositions which may be administered in a suitable time-release formulation are described in the aforementioned U.S. Pat. No. 4,762,717 and the patents cited therein. These include decapeptyl, buserelin, nafarelin, deslorelin, histrelin, gonadorelin and $[(Imbzl)-D-His^6-Pro^9-Net]GnRH$.

The dose of GnRH composition must be sufficient to completely suppress ovarian estrogen production, so that estrogen effects are predictably related to the administered estrogen. The amount of GnRH composition effective to achieve the desired suppression of ovarian estrogen production may readily be determined with respect to any given GnRH composition and for any given mammal. In the combined administration of an effective dose of GnRH composition, the dose range depends upon the particular GnRH composition used, but is in an amount effective to suppress LH and FSH. The effective dose ranges, as well as being compound specific, may also depend upon patient characteristics, such as age and weight. Further, the effective amount of GnRH composition also depends upon route of administration. Thus, administration by subcutaneous or intramuscular routes typically requires less GnRH composition than administration by transdermal or vaginal routes. An effective dose range of GnRH composition is thus determined by routine testing by one of skill in the art without undue experimentation. The GnRH composition may comprise a single active agent or a combination of two or more such agents. In general, it is expedient to administer the active GnRH composition in an amount between about 0.0001 and 10 mg/kg of body weight per day. It is understood in the art that this range may vary depending upon whether a GnRH antagonistic analogue or a GnRH agonistic analogue, or combination of the two, is administered.

GnRH compositions are in general absorbed very well across a wide variety of surfaces. Thus, subcutaneous, intramuscular, vaginal and transdermal routes of administration have all proven to be effective, and would be suitable for use in accordance with the present invention. In an embodiment of this invention, administration of the delivery system is made via the intramuscular route. Thus, the GnRH composition is administered via an intramuscular delivery system using an excipient which effects a slow degradation of the delivery system.

As previously noted, the use of a GnRH composition alone as a suitable method for contraception or for treatment of benign gynecological disorders had effectively been abandoned in view of the side effects attendant thereto. Many of the side effects of GnRH composition use reflect the hypoestrogenic state induced and can thus be prevented in accordance with the present invention by add-back estrogen therapy. Accordingly, a second component of a contraceptive regimen in accordance with the present invention is an effective amount of an estrogenic composition to prevent symptoms of estrogen deficiency, e.g., prevent symptoms and signs of the menopause, including adverse alterations in serum cholesterol.

As the add-back estrogen, a single-component natural or synthetic estrogen composition or a combination of such compositions can be used to maintain a constant systemic level. A substantial body of information exists concerning the effects of hormone replacement therapy after a natural or surgical menopause. Although more is known about the effects of conjugated equine estrogens (CEE) as estrogen replacement therapy (ERT) than any other agent, it is presently preferred that a single-component or two-component composition be employed.

As used herein, estrogenic compositions refer to both the natural and the synthetic materials. These materials are well known in the art. Natural and synthetic estrogenic compositions which can be used according to the invention described herein include natural estrogenic hormones and congeners, including but not limited to estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol and estrone potassium sulfate. Equine estrogens, such as equilelinin, equilelinin sulfate and estetrol, may also be employed.

Typical dose ranges for estrogenic compositions depend not only upon the choice of composition, but also upon the characteristics of the patient. For an adult human female patient administered estradiol, typical dose ranges are such that the serum level of estradiol is maintained at a level of about 25 to about 140 pg/ml. Most preferably, the serum level of estradiol is about 30 to about 50 pg/ml, which is significantly lower than the preferred serum level of 80 to 120 pg/ml called for by Crowley.

In accordance with the present invention, the effective dosage of an estrogenic composition is preferably delivered in the same delivery system as the GnRH composition, although the excipient composition and/or formulation may differ. The delivery system thus allows complete suppression of gonadotropins, removal of reproductive function of the ovaries, and complete suppression of ovarian steroidogenesis for the extended period of time for which the system is designed to be effective; at the same time, there is a replacement of sufficient levels of estrogen to minimize or eliminate the long-term side effects of GnRH composition administration.

The third component of the inventive regimen is a progestogen. Unlike the GnRH composition and estrogen replacement, which are administered at a continuous level for an extended period of time equal to the duration of the treatment cycle, in accordance with one embodiment of the present invention the progestogen component is present in an amount sufficient to provide elevated systemic levels for only a second, more limited period of time. Typically, the progestogen is administered for a period of time on the order of less than about ¼ to about ½ the period of time of administration of GnRH composition and estrogenic component. For typical formulations which are effective for periods of about two to about six months, this would amount to periods of progestogen administration in the range of about 15 days up to about 90 days (in the longer-acting formulations). It is contemplated, however, in accordance with the present invention that administration of progestogen for even shorter periods of time (e.g., as little as five days) would be effective in some formulations. Therefore, the second shorter period of time for administration of elevated amounts of progestogen in accordance with the present invention would typically fall within a range from an effective minimum of about five days up to an effective maximum of about ½ the duration of GnRH composition and estrogenic composition administration.

In accordance with this embodiment of the present invention, progestogen is provided for the second shorter period of time in an amount effective to induce a secretory endometrium and/or eliminate endometrial hyperplasia, which may occur during prolonged treatment with estrogenic compositions without a progestogen, for at least 5 to about 20 days, followed by a lower amount effective to decrease endometrial cell proliferation for the remainder, if any, of the period of progestogen administration. The progestogen is suitably delivered in the same delivery system as the GnRH composition and the estrogenic composition, although the excipient composition and/or formulation may differ to permit release of elevated levels of the progestogen over the first part of the second shorter time period.

Unlike the method proposed by Crowley, administration of progestogen in accordance with this embodiment of the present invention is generally not repeated every 28 days (corresponding to the length of the normal menstrual cycle). Rather, the progestogen component is provided in these preferred embodiments only for the initial phase of each extended treatment regimen. Suitably, a treatment cycle in accordance with the present invention comprises about two to about six months, and most preferably three or four months.

Suitable progestational agents (progestogens) for use in accordance with the present invention include but are not limited to dydrogesterone, ethynodiol diacetate, hydroxyprogesterone caproate, medroxyprogesterone acetate, norethindrone, norethindrone acetate, norethynodrel, norgestrel, progesterone, and megestrol acetate. Typical dose ranges for progestogens depend upon the choice of composition and the individual patient. For an adult human female administered progesterone, typical doses are administered to provide elevated serum levels of progesterone of from about 5 to about 20 ng/ml, and preferably about 5 to about 15 ng/ml, during the time interval of progestogen treatment for about 5 to about 20 contiguous days, and preferably about 10 to about 15 contiguous days, followed by doses to provide serum levels of progesterone of from about 0.5 to about 4 ng/ml, and preferably about 1 to about 2 ng/ml, for the remaining period, if any, of progestogen administration.

In accordance with an alternative embodiment of the present invention, progestogen is administered throughout the period of administration of GnRH composition and estrogenic component. The progestogen delivered over substantially the entire first period of time is in an amount effective to inhibit cell proliferation in the endometrium; this reduced amount would not be sufficient to induce a secretory endometrium and/or eliminate endometrial hyperplasia, which may occur during prolonged treatment with estrogenic compositions without a progestogen. Once again, typical dose ranges depend upon the choice of composition and the individual patient. For an adult human female administered progesterone, typical doses are administered (over the same extended time period as GnRH composition and estrogenic composition) to provide serum levels of progesterone of from about 0.5 to about 4 ng/ml, and preferably about 1 to about 2 ng/ml.

In accordance with yet another embodiment of the present invention, an androgenic composition is administered over the first period of time in conjunction with administration of GnRH composition, estrogenic composition and progestogen as previously described. The androgenic composition is administered in an amount effective to restore a patient's androgen levels to normal premenopausal levels, and in particular to maintain bone mineral density. Administration to oophorectomized women of the androgen, methyltestosterone, at an amount in the premenopausal range of testosterone has been shown to add significantly to the bone preserving action of ERT; women on the combined regimen actually increased their bone mass [Watts et al., "Effects of oral esterified estrogens and esterified estrogens plus androgens on bon mineral density in postmenopausal women, "*North American Menopause Society*, Meeting Abstract, (Montreal, Canada 1991)]. Restoration of a patient's normal androgen levels is desirable, as administration of other components of the formulations in accordance with the invention has the effect of reducing serum androgen levels, in some cases significantly. For purposes of the present invention, normal androgen levels are on the order of about 20 to about 80 ng/dl for testosterone and about 50 to about 250 ng/dl for androstenedione.

Suitable androgenic hormones for use in accordance with the present invention include but are not limited to testosterone, androstenedione, dihydrotestosterone, testosterone propionate, testosterone enanthate, testosterone cypionate, methyltestosterone, danazol, dromostanolone propionate, ethylestrenol, methandriol, nandrolone decanoate, nandrolone phenpropionate, oxandrolone, oxymethalone, stanozolol and testolactone. Typical dose ranges for androgenic hormones depend upon the choice of composition and the individual patient. For an adult human female administered testosterone, typical doses are administered to provide serum levels of testosterone of from about 20 ng/dl to about 80 ng/dl, and preferably about 40 to about 60 ng/dl.

In accordance with the present invention, the delivery vehicle of the invention provides for administration of GnRH composition, estrogenic composition, progestogen and optionally androgen by a subcutaneous, intramuscular, vaginal or transdermal route. The carrier vehicle for each component is selected from a wide variety of materials which are already known per se or may hereafter be developed which provide for controlled release of the compositions in the particular physiological environment. In particular, the carrier vehicle of the delivery system is selected such that near zero-order release of the components of the regimen is achieved. In the context of the present invention, the carrier vehicle should therefore also be construed to embrace particular formulations of the compositions which are themselves suitable for providing near zero-order release. A targeted steady-state release can be obtained by suitable adjustment of the design or composition of the delivery system.

One suitable formulation to achieve the desired near zero-order release of the components comprises injectable microcapsules or microspheres prepared from a biodegradable polymer, such as poly(dl-lactide), poly(dl-lactide-co-glycolide), polycaprolactone, polyglycolide, polylactic acid-co-glycolide, poly(hydroxybutyric acid), a polyortho-ester or a polyacetal. Injectable systems comprising microcapsules or microspheres of a diameter on the order of about 50 to about 500 $\mu$m offer advantages over other delivery systems. For example, they generally use less hormone and may be administered by paramedical personnel. Moreover, such systems are inherently flexible in the design of the duration and rate of separate drug release by selection of microcapsule size, drug loading and dosage administered. In addition, such microcapsules can be successfully sterilized with gamma irradiation.

Microcapsules are systems comprising a polymeric wall that encloses a liquid or solid core. The capsule wall usually does not react with the core material; however, it is designed to provide sufficient strength to enable normal handling without rupture while being sufficiently thin to allow a high core to wall volume ratio. The capsule contents remain within the wall until released by diffusion or other means that dissolve, melt, break, rupture or remove the capsule material. Preferably, the capsule wall can be made to degrade and decompose in suitable environments while diffusing the core material through the capsule wall to allow for its slow, prolonged delivery.

The mechanism of release in biodegradable microcapsules is a combination of drug diffusion and polymer biodegradation. Therefore, the rate and duration of release are determined by microcapsule size, drug content and quality, and polymer parameters, such as crystallinity, molecular weight and composition. In particular, adjustment in the amount of drug released is generally achieved by modification of capsule wall thickness, capsule diameter, or both. Detailed information concerning the design and use of microspheres and microcapsules is provided by, e.g., Lewis, D. H., "Controlled Release of Bioactive Agents from Lactide/Glycolide Polymers," in Jason & Langer (eds.), *Biodegradable polymers as drug delivery systems*, pp. 1–41 (1990), the entire disclosure of which is hereby incorporated by reference.

Several methods are currently available for preparing microcapsules. As discussed in Nuwayser, E. S. et al., "Microencapsulation of Contraceptive Steroids," in Zatuchni, G. L. et al. (eds.), *Long-acting contraceptive delivery systems*, pp. 64–76 (1984), the entire disclosure of which is hereby incorporated by reference, most of these methods can be classified under three major categories: coacervation, coagulation and air-suspension coating.

An exemplary material for use in the formulation of suitable microcapsules or matrix formulations is poly(dl-lactide-co-glycolide) as described in Lewis, D. H. and Tice, T. R., "Polymeric Considerations in the Design of Microencapsulation of Contraceptive Steroids," in Zatuchni, G. L. et al. (eds.), *Long-acting contraceptive delivery systems*, pp. 77–95 (1984), the entire disclosure of which is hereby incorporated by reference. The solvent evaporation process described therein is suitable for preparing microcapsules in a size range acceptable for administration by conventional syringe and needle; moreover, the yield or fraction of microcapsules within a desired size range can be selected and achieved with appropriate process adjustments. This enables the preparation of diffusional controlled-release formulations in which the duration of drug release is directly related to total surface area or microcapsule particle size. Another exemplary material is poly($\epsilon$-caprolactone) as described in Pitt, C. G. and Schindler, A., "Capronor—A Biodegradable Delivery System for Levonorgestrel," in Zatuchni, G. L. et al. (eds.), *Long-acting contraceptive delivery systems*, pp. 48–63 (1984), the entire disclosure of which is hereby incorporated by reference. Other biodegradable polymeric materials suitable for preparation of microcapsules for controlled (i.e., near zero-order) release would be readily determined through routine experimentation by those skilled in the art.

An alternative delivery system suitable for use in accordance with the present invention comprises fibers or filaments comprising the active agents and biodegradable or non-biodegradable polymers. Precision delivery systems can be mass-produced by this method; moreover, geometrically configured controlled-release devices can be produced by, e.g., wrapping drug-releasing fibers around conventional intravaginal rings or other intravaginal devices. Typically, fibrous delivery systems rely on membrane-moderated diffusion mechanisms to control the rate and duration of drug release. Monolithic drug-releasing fibers may be prepared by conventional spinning processes; when reservoir-type fibrous systems are desired, either a fast-releasing monolithic fiber is prepared and then coated with a rate-controlling sheath, or a coaxial spinning process is employed, in which the drug is extruded as the core of the fiber at the same time as the rate-controlling polymer sheath. Suitable fibers for providing zero-order release of the active agents and methods for the preparation thereof are described in Cowsar, D. E. and Dunn, R. L., "Biodegradable and Nonbiodegradable Fibrous Delivery Systems," in Zatuchni, G. L. et al. (eds.), *Long-acting contraceptive delivery systems*, pp. 145–163 (1984), the entire disclosure of which is hereby incorporated by reference.

Other suitable materials for preparation of such intravaginal devices include silicon-based materials, such as polydimethylsiloxanes, which have been employed to prepare capsule-type, matrix-type and microsealed drug delivery systems. For example, a suitable device may be prepared by coating a non-medicated silicone rubber core with a thin layer of silicone rubber (such as MDX-4-4210 Clean Grade Elastomer, available from Dow Corning) which contains micronized crystalline forms of the active agents. An implant of this type (for administration of estradiol-17$\beta$) is described in Ferguson, T. H. et al., "Compudose: An Implant System for Growth Promotion and Feed Efficiency in Cattle," *J. Controlled Release* 8, pp. 45–54 (1988), the entire disclosure of which is hereby incorporated by reference. Improved devices may be prepared by incorporating water-soluble carriers, such as sodium alginate, or by using additives, such as co-solvents or salts, which enhance the release rate of active agents from the polymer matrix.

In general, contraceptive vaginal rings may be designed as homogeneous mixtures of composition and silastic; as a core vaginal ring surrounded by silastic; as a shell ring with a core of silastic, surrounded by a layer of composition and silastic covered by a tube of silastic; as a band ring of inert silastic with a drug-containing band on the ring; or as a combination of the various designs to permit the specific release characteristics desired. In this regard, useful systems are described in the following: Jackanicz, T. M., "Vaginal Ring Steroid-Releasing Systems," pp. 201–212; Diczfalusy, E. and Landgren, B.-M., "Some Pharmacokinetic and Pharmacodynamic Properties of Vaginal Delivery Systems That Release Small Amounts of Progestogens at a Near Zero-Order Rate," pp. 213–227; and Roy, S. and Mishell, Jr., D. R., "Vaginal Ring Clinical Studies: Update," pp. 581–594, all in Zatuchni, G. L. et al. (eds.), *Long-acting contraceptive delivery systems* (1984), the entire disclosures of which are hereby incorporated by reference.

For transdermal delivery of the active agents, suitable pads or bandages are also well known in the art. Typically, these pads comprise a backing member defining one exterior surface, a surface of pressure-sensitive adhesive defining a second exterior surface, and disposed therebetween a reservoir containing the active agents confined therein. Suitable transdermal delivery systems are disclosed in U.S. Pat. Nos. 3,731,683 and 3,797,494 to Zafforoni and U.S. Pat. No. 4,336,243 to Sanvordeker et al., the entire disclosures of which are hereby incorporated by reference.

Other suitable formulations would be readily apparent to those of skill in the art. For example, with certain active agents, administration may be effected subcutaneously or intramuscularly with slowly-dissolving pellets of crystalline or microcrystalline materials, or directly as a crystalline or microcrystalline aqueous suspension. The important features are maintenance of near zero-order release of the drugs over the desired treatment periods, followed by a relatively rapid decrease in serum concentrations to low levels once the relevant portion of the treatment regimen has been completed.

The inventive regimen is designed to reduce the degree of adverse effects associated with the use of GnRH compositions, estrogen and progestogen in accordance with the heretofore known protocols, such as those of Crowley and Pike et al. For example, GnRH compositions have been recognized as having an adverse impact on bone metabolism. Bone mineral density (BMD) is known to fall after a natural or surgical menopause; the fall is most evident in regions of trabecular bone. A net loss of BMD has been seen in the majority of studies after 6 month of GnRH agonist treatment, well in excess of even the greatest rates of fall of approximately 1%/yr that have been reported in premenopausal women. This loss of BMD is secondary to the reduction in estrogens and androgens. In accordance with the present invention, ERT combined with a progestogen and optional androgen is administered to reduce BMD loss in postmenopausal women. The reduction in BMD loss is mirrored in a much reduced fracture risk in ERT treated postmenopausal women. Similarly, the ability of ERT to control hot flashes and other menopausal symptoms is also well documented. By combining GnRH composition therapy with appropriate levels of estrogen, progestogen and optionally androgen replacement therapy the effects of the hypoestrogenic state induced by the GnRH composition are prevented. One effect of the optional use of androgens is to enable a reduction in the dose of estrogen necessary to prevent loss of BMD.

An increased risk of cardiovascular disease has been a further concern with the long-term use of a GnRH composition, as such an increase has been associated with oophorectomy at a young age. According to the present invention, add-back estrogen is employed to reduce the risk of cardiovascular disease. As is the case when ERT is given to postmenopausal women, one reason for this reduction in risk is likely to be the beneficial effects of estrogen on serum cholesterol. GnRH agonists may have effects on cholesterol which are not mediated by their effects on serum estrogens. The GnRH plus add-back estrogen is predicted to result in a beneficial rise in high density lipoprotein cholesterol or HDLC (increase from add-back estrogen) and no change in low density lipoprotein cholestrol or LDLC (increase from GnRH agonist balanced by comparable decrease from add-back estrogen), a clearly beneficial overall effect. The addition of progestogen and optional androgen replacement may slightly increase LDLC and slightly decrease HDLC, but the overall predicted effect of the proposed regimen remains beneficial.

While estrogen thus has significant positive effects in conjunction with the use of a GnRH composition, it is nonetheless important to recognize the potential risks inherent in such treatment. For example, a substantial body of evidence has shown that ovarian hormones are critical factors in the etiology of breast cancer. Inducing a reversible "medical oophorectomy" through the use of a GnRH composition given at a dose sufficient to suppress ovarian function to postmenopausal levels in accordance with the present invention similarly achieves a major reduction in a woman's lifetime breast cancer risk relative to the use of COCs. Add-back therapy with low-dose estrogen and progestogen is, however, required to prevent harmful hypoestrogenic effects and to protect the endometrium. Thus, the present invention strives for an appropriate balance in the combined effect of a GnRH composition and the add-back hormone regimen so as to minimize subsequent breast cancer risk.

If there were no increased breast cancer risk from ERT and progestogen use in the postmenopausal period, then the prototype GnRH composition plus add-back estrogen plus progestogen regimen should substantially reduce breast cancer risk as it should simply be equivalent to temporary bilateral oophorectomy. A more cautious approach is to assume that the addition of add-back estrogen to the GnRH composition regimen causes some increase in breast cancer risk when compared to the use of GnRH composition alone, and that the addition of progestogen may increase the risk further. The addition of the optional androgen would have no effect on breast cancer risk.

An estimate of the effect of a preferred four-month prototype contraceptive (Example 1) on lifetime breast cancer risk is shown in Table 1. To estimate conservatively the effect on breast cancer risk of the prototype contraceptive regimen, it is assumed that the effect of the progestogen component is to quadruple the increased risk from the add-back estrogen on the days on which it is administered. Table 1 shows that lifetime breast cancer risk is predicted to be reduced in accordance with the present invention by 31% if used for 5 years and by 53% if used for 10 years.

Similarly, it is well-established that early menopause will substantially reduce endometrial cancer risk. Use of a GnRH composition at a dose sufficient to suppress ovarian function to postmenopausal levels similarly is expected to achieve a substantial reduction in a woman's risk of endometrial cancer. The addition of add-back estrogen therapy to the GnRH composition may, however, increase the endometrial cancer risk when compared to use of the GnRH composition alone. Epidemiological studies of postmenopausal women show that "low-dose" ERT increases risk of endometrial cancer significantly less than "high-dose" ERT. Therefore, in accordance with the present invention, low-dose add-back estrogen with addition of a progestogen only infrequently is proposed to reduce this risk. An estimate of the effect of a preferred prototype contraceptive (Example 1) on lifetime endometrial cancer risk is shown in Table 1. Calculations suggest that there will be modest lifetime reduction in risk of endometrial cancer with even short-term use of the proposed regimen.

Endometrial hyperplasia is a significant clinical concern with ERT use in postmenopausal women. Progestogen therapy for 5–20 days (preferably, 10–15 days) will control endometrial hyperplasia induced by add-back estrogen and achieve the desired histological changes in the endometrium. Such a regimen is not required every month; the addition of further courses of progestational agent provides a further benefit to the endometrium, and may further improve bone metabolism, but is likely to have a deleterious effect on heart disease risk and breast cancer risk as discussed above. While a small proportion of women may develop hyperplasia if progestogens are not given every 28-day cycle, few will develop symptoms. Therefore, the present invention in preferred embodiments calls for a progestogen treatment course only every few months to eliminate any hyperplasia that has developed. A lower dose progestogen may be given for a more extended period of time to reduce endometrial cell proliferation and subsequent endometrial cancer risk.

Finally, the present invention is designed to reduce the risk of ovarian cancer. Protective risk factors that have been consistently found in epidemiological studies of ovarian cancer are early menopause, high parity and use of COCs. With increasing parity or increasing duration of COC use ovarian cancer risk decreases steadily. The suppression of ovulation by GnRH compositions should protect against ovarian cancer to the same extent as do COCs. The addition of ERT plus progestogen and optionally androgen to the GnRH composition regimen should have no effect on this reduced risk.

Table 1 shows the predicted relative risks for ovarian cancer of using the prototype contraceptive for 5, 10 or 15 years at premenopausal ages. The calculations were based on using the regimen at any time during the premenopausal period. Use for 5 years is predicted to reduce the lifetime risk of ovarian cancer by as much as 41%; use for 10 years should reduce the risk by 67%.

TABLE 1

Predicted Relative Reduction in Lifetime Risk of Cancer With Prototype Contraceptive (Example 1)

| Duration of Regimen (years) | 5 | 10 | 15 |
|---|---|---|---|
| Breast | 31% | 53% | 70% |
| Endometrium | 18% | 33% | 45% |
| Ovary | 41% | 67% | 84% |

An alternative preferred three-month regimen is predicted to provide the same protection for the ovary, increased protection for the endometrium and decreased protection for the breast.

The following examples will serve to illustrate the invention without in any way being limiting thereon.

EXAMPLE 1

This example describes a delivery system for intramuscular administration over a 4-month duration. The delivery system administers a GnRH composition (buserelin), a natural estrogenic steroid (estradiol) and a natural progestogenic steroid (progesterone), such that the amount of GnRH composition is sufficient to suppress LH and FSH secretion during the entire period of administration, with the serum level of estradiol being maintained at about 40 pg/ml. The buserelin is provided at a dose of 6.6 mg, which is sufficient to maintain serum levels on the order of 30 pg/ml throughout the treatment cycle. The estradiol is provided in a dose of 10 mg. Both the buserelin and estradiol are provided in the form of microspheres prepared from a copolymer of lactide and glycolide; as is well known in the art, this copolymer provides for an effective time-release formulation which is biodegradable. The serum level of progesterone is maintained at about 5 to 10 ng/ml for the first 10 to 15 days after administration; thereafter, the serum level drops below 5 ng/ml before reaching a baseline level of below about 1 ng/ml for the balance of the 4-month period. The progesterone is provided in a dose of 150 mg in the form of the micronized drug.

Optionally, androgen is provided in a dose of 10 mg of testosterone. The serum level of testosterone is maintained at about 50 ng/dl. The testosterone is provided in the form of microspheres prepared from a copolymer of lactide and glycolide.

EXAMPLE 2

This example describes a vaginal ring. A shell ring of estradiol releases about 180 µg/day and thereby achieves serum levels of about 40 pg/ml for its 120 days of use. Buserelin is also released to achieve serum levels of about 30 pg/ml. In the shell ring, a band is provided containing medroxyprogesterone acetate in silastic without a shell, to release about 1 mg/day of medroxyprogesterone acetate over about 10–15 days. The vaginal ring is replaced with a fresh ring about every 120 days.

While there have been shown and described the fundamental novel features of the invention, it will be understood that various omissions, substitutions and changes in the form and details of the contraceptive devices illustrated may be made by those skilled in the art without departing from the spirit of the invention. It is the intention, therefore, to be limited only as indicated by the scope of the following claims.

What is claimed is:

1. A composition comprising:
   a slow-release formulation of a gonadotropin hormone releasing hormone composition which maintains serum level of said gonadotropin hormone releasing hormone composition in a female mammal at a level effective to suppress ovarian estrogen and progesterone production over a first period of time, said GnRH composition being administered so as to provide between about 0.0001 and about 10 mg/kg of body weight per day;
   a slow-release formulation of an estrogenic composition which maintains serum level of said estrogenic composition over said first period of time at a level effective to prevent symptoms of estrogen deficiency, said level being equivalent to a serum level of estradiol of between about 25 and about 140 pg/ml; and
   a slow-release formulation of a progestogen which maintains serum level of said progestogen at a first level effective to induce a secretory endometrium for at least 5 to about 20 days and at a second lower level effective to decrease endometrial cell proliferation for a remainder, if any, of a second period of time, said second period of time being substantially shorter than and running simultaneously with a portion of said first period of time, said first level being equivalent to a serum level of progesterone of between about 5 and about 20 ng/ml and said second level being equivalent to a serum level of progesterone of between about 0.5 and about 4 ng/ml.

2. A composition according to claim 1, wherein said gonadotropin hormone releasing hormone composition is selected from the group consisting of gonadotropin hormone releasing hormone, gonadotropin hormone releasing hormone analogues, gonadotropin hormone releasing hormone agonists, gonadotropin hormone releasing hormone antagonists and mixtures thereof.

3. A composition according to claim 2, wherein said gonadotropin hormone releasing hormone composition is a gonadotropin hormone releasing hormone agonist selected from the group consisting of leuprolide acetate, goserelin, decapeptyl, buserelin, nafarelin, deslorelin, histrelin, gonadorelin, [(Imbzl)-D-His$^6$-Pro$^9$Net]GnRH and mixtures thereof.

4. A composition according to claim 1, wherein said estrogenic composition is selected from the group consisting of estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol, estrone potassium sulfate, equilelinin, equilelinin sulfate, estetrol and mixtures of two or more thereof.

5. A composition according to claim 1, wherein said progestogen is selected from the group consisting of dydrogesterone, ethynodiol diacetate, hydroxyprogesterone caproate, medroxyprogesterone acetate, norethindrone, norethindrone acetate, norethynodrel, norgestrel, progesterone, megestrol acetate and mixture of two or more thereof.

6. A composition according to claim 1, wherein said first period of time is about two months to about six months.

7. A composition according to claim 6, wherein said first period of time is about three months to about four months.

8. A composition according to claim 1, wherein said second period of time is about 5 days to about 90 days.

9. A composition according to claim 8, wherein said second period of time is less than about ¼ to about ½ of said first period of time.

10. A composition according to claim 1, for administration by a subcutaneous, intramuscular, vaginal or transdermal route.

11. A composition according to claim 1, further comprising:
    a slow-release formulation of an androgenic hormone which maintains serum level of said androgenic hormone over said first period of time at a level effective to restore androgen levels to normal premenopausal levels for a patient, said level being equivalent to a serum level of testosterone of between about 20 and about 80 ng/dl.

12. A composition according to claim 11, wherein said androgenic hormone is selected from the group consisting of testosterone, androstenedione, dihydrotestosterone, testosterone propionate, testosterone enanthate, testosterone cypionate, methyltestosterone, danazol, dromostanolone propionate, ethylestrenol, methandriol, nandrolone decanoate, nandrolone phenpropionate, oxandrolone, oxymethalone, stanozolol and testolactone.

13. A composition comprising:
    a slow-release formulation of a gonadotropin hormone releasing hormone composition which maintains serum level of said gonadotropin hormone releasing hormone composition in a female mammal at a level effective to suppress ovarian estrogen and progesterone production over a period of time, said GnRH composition being administered so as to provide between about 0.0001 and about 10 mg/kg of body weight per day;
    a slow-release formulation of an estrogenic composition which maintains serum level of said estrogenic composition over said period of time at a level effective to prevent symptoms of estrogen deficiency, said level being equivalent to a serum level of estradiol of between about 25 and about 140 pg/ml; and a slow-release formulation of a progestogen which maintains serum level of said progestogen over said period of time at a level effective to decrease endometrial cell proliferation, said level being equivalent to a serum level of progesterone of between about 0.5 and about 4 ng/ml.

14. A composition according to claim 13, wherein said gonadotropin hormone releasing hormone composition is selected from the group consisting of gonadotropin hormone releasing hormone, gonadotropin hormone releasing hormone analogues, gonadotropin hormone releasing hormone agonists, gonadotropin hormone releasing hormone antagonists and mixtures thereof.

15. A composition according to claim 14, wherein said gonadotropin hormone releasing hormone composition is a gonadotropin hormone releasing hormone agonist selected from the group consisting of leuprolide acetate, goserelin, decapeptyl, buserelin, nafarelin, deslorelin, histrelin, gonadorelin, [(Imbzl)-D-His$^6$-Pro$^9$-Net]GnRH and mixtures thereof.

16. A composition according to claim 13, wherein said estrogenic composition is selected from the group consisting of estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol, estrone potassium sulfate, equilenin, equilelinin sulfate, estetrol and mixtures of two or more thereof.

17. A composition according to claim 13, wherein said progestogen is selected from the group consisting of dydrogesterone, ethynodiol diacetate, hydroxyprogesterone caproate, medroxyprogesterone acetate, norethindrone, norethindrone acetate, norethynodrel, norgestrel, progesterone, megestrol acetate and mixtures of two or more thereof.

18. A composition according to claim 13, wherein said period of time is about two months to about six months.

19. A composition according to claim 13, wherein said period of time is about three months to about four months.

20. A composition according to claim 13, for administration by a subcutaneous, intramuscular, vaginal or transdermal route.

21. A composition according to claim 13, further comprising:
a slow-release formulation of an androgenic hormone which maintains serum level of said androgenic hormone over said first period of time at a level effective to restore androgen levels to normal premenopausal levels for a patient, said level being equivalent to a serum level of testosterone of between about 20 and about 80 ng/dl.

22. A composition according to claim 21, wherein said androgenic hormone is selected from the group consisting of testosterone, androstenedione, dihydrotestosterone, testosterone propionate, testosterone enanthate, testosterone cypionate, methyltestosterone, danazol, dromostanolone propionate, ethylestrenol, methandriol, nandrolone decanoate, nandrolone phenpropionate, oxandrolone, oxymethalone, stanozolol and testolactone.

23. A method for preventing conception in a mammal or for treating benign gynecological disorders, comprising:

administering a gonadotropin hormone releasing hormone composition for a first period of time in an amount effective to maintain serum level of said gonadotropin hormone releasing hormone composition at a level effective to suppress ovarian estrogen and progesterone production, said GnRH composition being administered so as to provide between about 0.0001 and about 10 mg/kg of body weight per day;

simultaneously administering an estrogenic composition in an amount effective to maintain serum level of said estrogenic composition over said first period of time at a level effective to prevent symptoms of estrogen deficiency, said level being equivalent to a serum level of estradiol of between about 25 and about 140 pg/ml; and administering a progestogen for a second, shorter period of time in an amount effective to maintain serum level of said progestogen at a first level effective to induce a secretory endometrium for at least 5 to about 20 days and at a second lower level effective to decrease endometrial cell proliferation for a remainder, if any, of said second period of time, said second period of time being substantially shorter than and running simultaneously with a portion of said first period of time, said first level being equivalent to a serum level of progesterone of between about 5 and about 20 ng/ml and said second level being equivalent to a serum level of progesterone of between about 0.5 and about 4 ng/ml.

24. A method according to claim 23, further comprising administering an androgenic composition over said first period of time in an amount effective to restore effective androgen level to a normal premenopausal level for a patient, said level being equivalent to a serum level of testosterone of between about 20 and about 80 ng/dl.

25. A method according to claim 23, wherein said first period of time is about two months to about six months.

26. A method according to claim 23, wherein said first period of time is about three months to about four months.

27. A method according to claim 23, wherein said second period of time is about 5 days to about 90 days.

28. A method according to claim 23, wherein said second period of time is less than about ¼ to about ½ said first period of time.

29. A method for preventing conception in a mammal or for treating benign gynecological disorders, comprising:

administering a gonadotropin hormone releasing hormone composition for a period of time in an amount effective to maintain serum level of said gonadotropin hormone releasing hormone composition at a level effective to suppress ovarian estrogen and progesterone production, said GnRH composition being administered so as to provide between about 0.0001 and about 10 mg/kg of body weight per day;

simultaneously administering an estrogenic composition in an amount effective to maintain serum level of said estrogenic composition over said period of time at a level effective to prevent symptoms of estrogen deficiency, said level being equivalent to a serum level of estradiol of between about 25 and about 140 pg/ml; and simultaneously administering a progestogen in an amount effective to maintain serum level of said progestogen over said period of time at a level effective decrease endometrial cell proliferation, said level being equivalent to a serum level of progesterone of between about 0.5 and about 4 ng/ml.

30. A method according to claim 29, further comprising administering an androgenic composition over said first period of time in an amount effective to restore effective androgen level to a normal premenopausal level for a patient, said level being equivalent to a serum level of testosterone of between about 20 and about 80 ng/dl.

31. A method according to claim 29, wherein said period of time is about two months to about six months.

32. A method according to claim 29, wherein said period of time is about three months to about four months.

* * * * *